US005447849A

United States Patent [19]

Toora

[11] Patent Number: 5,447,849

[45] Date of Patent: Sep. 5, 1995

[54] GROWTH MEDIA AND ASSAY FOR YERSINIA ENTEROCOLITICA

[75] Inventor: Syed Toora, Charlottetown, Canada

[73] Assignee: Prince Edward Island Food Technology Center, Charlottetown, Canada

[21] Appl. No.: 118,727

[22] Filed: Sep. 10, 1993

[51] Int. Cl.[6] .......................... C12N 1/00; C12N 1/20; C12N 5/00; C12N 5/02

[52] U.S. Cl. .................................. 435/34; 435/240.3; 435/240.31; 435/252.1

[58] Field of Search .................. 435/29, 32, 34, 253.6, 435/252.1, 240.3, 240.31

[56] References Cited

PUBLICATIONS

Altovfer, et al. J Clinical Microbiology. vol. 22, No. 4, pp. 478–480 (1985).

Difco Manual, 10th Ed. Difco Laboratories, Detroit, Mich. pp. 430–431, 1055–1056, 1115, 1141–1143 (1984).

Greenwood, et al. Epid. Inf. v 101 pp. 53–58 (1988).

Difco Manual 10th Ed. Difco Laboratories Detroit, Mich. p. 1020 (1984).

PEI Food Tech Center Aug. 3, 1993 (see 3 pages).

Wauters et al: "New enrichment method for isolation of pathogenic Yersinia enterocolitica serogroup 0:3 from Pork", Applied and Environmental Microbiology 34, (4), 851–854 (1988).

Schiemann: "Development of a two-step enrichment procedure for recovery of Yersinia enterocolitica from food", Applied and Environmental Microbiology, 43, (1), 14–27 (1982).

Kounev: "Procedures for recovery of stressed and injured cells of Yersinia enterocolitica from meat and meat products", Journal of Food Protection, 52, (5), 360–362 (1989).

Landgraf et al: "An improved enrichment procedure for the isolation of Yersinia enterocolitica and related species from milk", Journal of Food Protection,56 (5) 447–450 (1993).

Kounev: "Effects of enrichment medium and incubation temperature on recovery of Yersinia enterocolitica from cooked sausage", Journal of Food Protection, 52 (11), 818–820 (1989).

*Primary Examiner*—William H. Beisner
*Assistant Examiner*—Jane A. Williams
*Attorney, Agent, or Firm*—Cushman, Darby & Cushman

[57] ABSTRACT

A growth medium for enhancing the selective growth of most serotypes of *Yersinia enterocolitica* obtained from environmental and clinical samples. The medium comprises an effective amount of a composition of a suitable nutrient source for *Y. enterocolitica* and an effective antimicrobial amount of 5-chloro-2-(2,4-dichlorophenoxy) phenol. The medium components may be provided as a dry powder for use in an aqueous formulation. An improved assay and isolation method is provided.

2 Claims, No Drawings

GROWTH MEDIA AND ASSAY FOR YERSINIA ENTEROCOLITICA

FIELD OF THE INVENTION

This invention relates to growth media for enhancing the growth of *Yersinia enterocolitica* in food samples and to methods for the assay of *Y. enterocolitica.*

BACKGROUND OF THE INVENTION

One of the most important and dangerous types of foodborne infections which has been recognized recently is yersiniosis. This is caused by the bacteria *Yersinia enterocolitica*. The genus Yersinia is widespread in the environment and can grow at refrigeration temperatures to cause problems in chilled food products stored for extended periods of time. There is concern from medical authorities that the food supply ought to be monitored for the presence of this microorganism, although the food industry is not yet routinely monitoring the presence of Yersinia in products. However, many authorities expect that Yersinia will become as important as Listeria is now.

The genus Yersinia is composed of a collection of Gram-negative, facultative anaerobic bacilli that share with other genera of the family Enterobacteriaceae a number of common morphologic, biochemical and serologic features. At present 11 species are recognized within this genus, three of which (*Y. pestis, Y. pseudotuberculosis, Y. enterocolitica*) have been shown unquestionably to be human pathogens (1,2). Yersinia are known to inhabit a wide range of animal and environmental sources, with some species displaying a host-specific tropism for colonization and/or infection. An interesting characteristic of most Yersinia spp. is their temperature-dependent expression of a number of phenotypic traits such as motility, biochemical properties and virulence-associated markers (3).

*Y. enterocolitica* is the most common agent of this genus recovered from patients and is usually associated with sporadic cases of gastroenteritis and mesenteric lymphadenitis. In the past two decades there has been a dramatic increase in the frequency of the isolation of this organism from both clinical and nonclinical specimens (4). In several countries, including the Netherlands, Belgium, Canada, and Australia, *Y. enterocolitica* has surpassed Shigella and rivals Salmonella and Campylobacter as a cause of acute bacterial gastroenteritis (5,6). Extra-intestinal illnesses attributed to *Y. enterocolitica* have been reported and include bacteraemia, arthritis, pharyngitis and pyomyositis (1,3). There are over 50 serotypes in this species; however, only five, designated 0:3, 0:5, 27; 0:6,30; 0:8 and 0:9, are generally regarded as pathogenic for humans (7).

Among the pathogenic serotypes, 0:3 and 0:9 have been commonly associated with *Y. enterocolitica* strains recovered from Europe, Scandinavia and Canada. Previously in the United States, serotypes 0:8 and 0:5, 27 were the predominating serotypes. However, Bottone (8) and Shayegani et al. (9) recently reported on the emergence of serotypes 0:3 in New York City and State, indicating changes in the U.S. pattern.

Yersinia has often been described as a food-borne pathogen (10,11), a deduction supported by descriptions of outbreaks in which some common vehicle was likely (12,13) and by the fact that a food animal, swine, is a reservoir of the common pathogenic serotype 0:3.

Geographic differences in the frequency and distribution of *Y. enterocolitica* infection are apparent. In Europe, Sporadic infections caused by serotypes 0:3 and 0:9 are common (5,14), but outbreaks of disease are rare. In the United States, sporadic disease is associated with multiple serotypes and is relatively uncommon (15,16), but five outbreaks have been caused by serotype 0:8. Transmission of this pathogenic bacteria to man appears to be mainly via the digestive tract, and may include the ingestion of contaminated food, contact with an infected animal, and person-to-person transmission through hand-to-mouth contact (17).

Thus, *Y. enterocolitica* has recently emerged as an important and dangerous foodborne pathogenic bacteria, the causative agent of yersiniosis, which is capable of growth at refrigeration temperature in various foods.

*Y. enterocolitica* infection of humans is due either to strains circulating from person to person or to strains found in foods or in other environmental sources that infect humans by the oral route (17).

One of the major problems in identifying the vehicle of transmission for yersiniosis outbreaks and identification of *Y. enterocolitica* as the causative agent of infection is the lack of appropriate isolation media.

The inability to identify the vehicle of transmission for yersiniosis outbreaks and delayed recognition of *Y. enterocolitica* is mainly attributed to the lack of appropriate isolation media and techniques with consequent lack of awareness of its presence in clinical specimens and foods (18). *Y. enterocolitica* strains show a marked degree of variability in their ability to grow on routinely-used enteric media, hence, those media are inadequate for primary isolation (3,19). Laboratory methods first used for recovery of *Y. enterocolitica* from foods were based primarily on cold enrichment techniques previously described for examination of faeces (20,21) and there have been few improvements since. Isolation of *Y. enterocolitica* from food is more difficult than from faeces taken from patients with active infections in that the number of Yersinia may be smaller, and the background flora is likely to be greater in both number and variety. Pai et al. (22) have concluded that cold enrichment is not essential for recovery of *Y. enterocolitica* from stool specimens taken from patients with symptoms and VanNoyan et al. (23) suggested that the additional recoveries obtained by cold enrichment were types of *Y. enterocolitica* that were not clinically important. In the case of foods, however, enrichment provides the only certain way for selecting out low number of Yersinia from the total microbial population.

Phosphate-buffered saline (PBS) has been a common cold-enrichment medium for both faeces and foods, Vanpee and Stragier (24) suggested that a rich broth such as trypticase soy broth is preferred for cold-enrichment.

Kounev (25) reported that phosphate-buffered saline (pH 7.6) was the best medium for the recovery of heat-injured cells of *Y. enterocolitica* serotype 0:3 from cooked sausage when incubated at 25° C. for 24–48 h. Incubation at 4° C. appeared to present an additional stress factor and more nutritive media interfered with the isolation of *Y. enterocolitica.*

Due to the long time periods required for cold-enrichment, there have been various efforts to devise selective enrichments which could be incubated for shorter times at higher temperatures. Inone and Kurose (26) used selenite medium with Novobiocin at 37° C. with less success than cold-enrichment. Lee et al. (27)

described two modified selenite media incubated at 22° C. that were effective for recovery of certain strains of *Y. enterocolitica.*

There have been only a few attempts to devise two-step enrichment techniques for recovery of *Y. enterocolitica* from raw milk. Vidon and Delmas (28) also obtained greater recovery from raw milk by using selective enrichment of their own formulation incubated at 28° C. for 48 hours after cold enrichment for 1 month. A selenite-malachite green ticarcillin enrichment without added nutrient was recommended by Lee et al. (29), especially for the recovery of the more fastidious strains from meat. Schiemann (18) described a two-step procedure, involving pre-enrichment in yeast-extract rose bengal (YER) broth, followed by selective enrichment in bile-oxalate-sorbose (BOS) medium for the isolation of *Y. enterocolitica* from foods.

The major disadvantages of BOS medium are:

(a) The complexity of its manufacture and that it is not yet commercially available; and (b) there is no evidence to show that this medium can recover the heat-and cold-injured cells of *Y. enterocolitica.*

Several other methods or modification of the existing methods have been proposed but are less widely used. Wauters et al. (30) have recommended a new enrichment methodology for the recovery of the most pathogenic serotype (0:3) from meat by using three selective agents, triclosan, ticarcillin and potassium chlorate, but this study does not explain whether the selective supplements are inhibiting other background microorganisms or enhancing the growth of *Y. enterocolitica*. Also the inhibitory action of these selective supplements are not shown against other background flora in this study.

A new three-step procedure (TSP) for the recovery of *Y. enterocolitica* 0:3 from frozen meat, salted and dried, meat products and cooked perishable sausages has been developed by Kouner (31). The TSP is based mainly on enrichment in 0.15M phosphate-buffered saline at 25° C.

The media and method used in the above studies are applicable only for the recovery of *Y. enterocolitica* serotype 0:3. No information is available for the efficiency of the above media and methods for the recovery of *Y. enterocolitica* serotypes other than 0:3.

Landgraf et al. (32) recommended an improved enrichment procedure for recovery of *Y. enterocolitica* from milk by modification of trypticase soy broth (TSB) with addition of polymyxin B and novobiocin. Not enough evidence has been published to show that this medium has inhibitory action against other Gram-negative bacteria or enhances the growth of all serotypes of *Y. enterocolitica*. This procedure and medium has been studied for the recovery of *Y. enterocolitica* only from milk and the author has also indicated the difficulties in the recovery of *Y. enterocolitica* from the raw milk because of the presence of other background microorganisms. All the media and procedures mentioned above have the disadvantages of either a long incubation time or complexity of preparation. As a result, none of the above media are commercially available.

The disadvantages of other techniques such as polymerase chain reaction (PCR) and DNA probes are that these techniques cannot detect low initial cell numbers in the sample or differentiate between the dead and live cells. Due to the high degree of similarities between the genetic material of most Gram-negative bacteria and being very much prone to contamination, the use of these techniques may lead to a false positive reaction.

Thus to date, no simple, selective, enrichment broth medium is available which is efficient for the isolation and recovery of all serotypes of *Y. enterocolitica* from environmental and clinical samples.

REFERENCE LIST

The present specification refers to the following publications, each of which is incorporated herein by reference.

PUBLICATIONS

1. Cornelis, G.; Laroche, Y.;Bulligand, G.; Sory, M. P. and Wauters, G. 1987. *Yersinia enterocolitica* is a primary model for bacterial invasiveness. Rev. Infect. Dis 9: 64-87.

2. Wauters, G.; Janssens, M.; Steigerwalt, A.G. and Brenner, D. J. 1988. *Yersinia mollaretii* sp. nov. and Yersinia bercovieri formerly called Yersinia enterocolitica biogroups 3A and 3B. Int. J. Syst. Bacteriol. 38: 424-429.

3. Bottone, F.J. 1977. *Yersinia enterocolitica:* a panoramic view of a charismatic microorganism. Crit. Rev. Microbiol. 5: 211-241

4. Mollaret, M. H.; Bercovier, M.; Alkonso, J. M. 1979. Summary of the data received at the WHO Reference Center for *Yersinia enterocolitica*. Contrib. Microbiol. Immunol. 5: 174-184.

5. Hoogkamp-Korstanje, J. A.; deKoning, J.; Samsom, J. P. 1986. Incidence of human infection with *Yersinia enterocolitica* serotypes 0:3–0:8 and 0:9 and the use of indirect immunoflouorescence in diagnosis. J. infect. Dis. 153: 138-141.

6. Marriott, D. J.; Taylor, S.; Dorman, D. C. 1985. *Yersinia enterocolitica* infection in children. Med. J. Aust. 143: 489-492.

7. Wauters, G.; Kandolo, K. and Janssens, M. 1987. Revised biogrouping scheme of *Yersinia enterocolitica*. Cont. Microbiol. Immunol. 9: 14-21.

8. Bottone, E. J. 1983. Current trends of *Yersinia enterocolitica* isolates in the New York City area. J. Clin. Microbiol. 17: 63-67.

9. Shayegani, M.; DeForge, I.; Glynn, D. M. and Root, T. 1981. Characteristics of *Yersinia enterocolitica* and related species isolated from human, animal and environmental source. J. Clin Microbiol. 14: 304-312.

10. Lee, W. H.; Vanderzant, C. and Stern, N. 1981. The occurrence of *Yersinia enterocolitica* in foods. In E. J. Bottone (ed), *Yersinia enterocolitica* pp. 162-171. CRC Press, Boca Raton, Fla.

11. Morris, G. K. and Feeley, J. C. 1976. *Yersinia enterocolitica*: a review of its role in food hygiene. Bull. W. H. O. 54: 79-85.

12. Asakawa, Y., Akahane, S.; Kagata, N.; Moguchi, M.; Sakazak, R. and Tamura, K. 1973. Two community outbreaks of human infection with *Yersinia enterocolitica*. J. Hyg. 71: 715-723.

13. Olsousky, Z. 1975. Mass occurrence of *Yersinia enterocolitica* in two establishments of collective care of children. J. Hyg. Epidemiol. Microbiol. Immunol. 19: 22-29.

14. Van Noyen, R.; Vandepitte, J.; Wauters, G.; Seldershaghs, R. 1981. *Yersinia enterocolitica*: its isolation by cold enrichment from patient and healthy subject. J. Clin. Pathol. 34: 1052-1056.

15. Shayegani, M.; DeForge, I.; McGlynn, D. M.; Root, T. 1981. Characteristic of *Yersinia enterocolitica* and related species isolated from human, animal and environmental sources. J. Clin. Microbiol. 14: 304-312.

16. Snyder, J. D.; Christenson, E.; Feldman, R. A. 1982. Human *Yersinia enterocolitica* infections in Wisconsin: Clinical, laboratory and epidemiological features. Am. J. Med. 72: 768-774.

17. Hurvell, B.; Danielsson-Tham, M. L.; Olsson, E. 1981. Zoonotic aspects of *Yersinia enterocolitica* with special reference to its ability to grow at low temperature, in "Psychrotrophic Microorganism in Spoilage and Pathogenicity". Eds. T. A. Roberts; G. Hobbs; J. H. B. Christian and N. Skovgaard. p. 393–399. Academic Press.

18. Schiemann, D. A. 1982. Development of a two-step enrichment procedure for recovery of *Yersinia enterocolitica* from food. Appl. Environ. Microbiol. 43, p. 14–27.

19. Bowen, J. H. and Kominos, S. D. 1979. Evaluation of a pectin agar medium for isolation of *Yersinia enterocolitica* within 48 hours. Am. J. Clinical. pathol. 72: 586-590.

20. Eiss, J. 1975. Selective culturing of *Yersinia enterocolitica* at low temperature. Scand. J. Infect. Dis. 7: 249-251.

21. Greenwood, J. R.; Flanigan, S. M., Pickett, M. J. and Martin, W. J. 1975. Clinical isolation of *Yersinia enterocolitica*: cold temperature enrichment. J. Clin. Microbiol. 2: 559-560.

22 . Pai, C. H.; Sorger, S.; Lafleur, L.; Lackman, L.; and Marks, M. I. 1979. Efficacy of cold enrichment techniques for recovery of *Yersinia enterocolitica* from human stool. J. Clin. Microbiol. 9: 712-715.

23. VanNoyen, R.; Vandepitte, J. and Wauters, G. 1980. Nonvalue of cold enrichment of stool for isolation of *Yersinia enterocolitica* serotypes 3 and 9 from patients. J. Clin. Microbiol. 1: 127-131.

24. VanPee, W. and Stragier, J. 1979. Evaluation of some cold enrichment and isolation media for the recovery of *Yersinia enterocolitica*. Antonie VanLeenwenhoek. J. Microbiol. Serol. 45: 405-477.

25. Kounev, Z. 1989. Effect of enrichment medium and incubation temperature on recovery of *Yersinia enterocolitica* from cooked sausage. J. Food Protec. 52: 818-820.

26. Inoue, M. and Kurose, M. 1975. Isolation of *Yersinia enterocolitica* from cow's intestinal contents and beef meat. Jpn. J. Vet. Sci. 37: 91-93.

27. Lee, W. H.; Harris, M. E.; McClain, D.; Smith, R. E. and Johnston, R. W. 1980. Two modified selenite media for the recovery of *Yersinia enterocolitica* from meats. Appl. Environ. Microbiol. 39: 205-209.

28. Vidon, D. J. M. and Delmas, C. L. 1981. Incidence of *Yersinia enterocolitica* in raw milk in Eastern France. Appl. Environ. Microbiol. 43: 355-359.

29. Lee, W. H.; Harris, M. E.; McClain, D.; Smith, R. E. and Johnston, R. W. 1980. Two modified selenite media for the recovery of *Yersinia enterocolitica* from meats. Appl. Environ. Microbiol. 39: 205-209.

30. Wauters, G.; Goossens, V.; Janssens, M. and Vandepitte, J. 1988. New enrichment method for isolation of pathogenic *Yersinia enterocolitica* serogroup 0:3 from pork. Appl. Environ. Microbiol. 851-854.

31. Kounev, Z. 1989. Procedures for recovery of stressed and injured cells of *Yersinia enterocolitica* from meat and meat products. J. Food Protec. 52: 360-362.

32. Landgrad, M.; Iaria, S. T. and Falcao, D. P. 1993. An improved enrichment procedure for the isolation of *Y. enterocolitica* and related species from milk. J. Food Protection 56. 447-450

SUMMARY OF THE INVENTION

Surprisingly, I have found that a specific antimicrobial agent has selective activity against some microorganisms, while having no or little effect against all serogroups of *Y. enterocolitica* to the extent that efficacious and useful growth and isolation media for *Y. enterocolitica* can be readily obtained.

Thus, it is an object of the present invention to provide a medium for the rapid and efficient isolation of *Y. enterocolitica* from various sources, from other background microorganisms.

It is a further object of the invention to provide a medium which provides growth of most, if not all serotypes of *Y. enterocolitica*.

It is a yet further object of the invention to provide a medium of relatively simple formulation, of straightforward use in the laboratory and low in cost.

Thus, the invention provides in its broadest aspect basic formulations which will inhibit the growth of most Gram-positive and Gram-negative bacteria, while enhancing the growth of most *Y. enterocolitica* spp.

Accordingly, in its broadest aspect the invention provides a medium for enhancing the growth of the pathogen *Y. enterocolitica* in a product contaminated with the pathogen, said medium having an effective amount of a composition comprising a suitable nutrient source for *Y. enterocolitica* and an effective antimicrobial amount of 5-chloro-2-(2,4-dichlorophenoxy) phenol.

A suitable nutrient source comprises a source of nitrogen, such as ammonium salts, amino acids, peptides and proteolytic digests of protein, living tissue extracts such as, for example, yeast extract, plant extract, meat extract and fish extract, bile salts and constituents thereof and alkali metal chlorides and alkaline earth metal chlorides.

In a preferred aspect, the invention provides a medium for enhancing the growth of the pathogen *Y. enterocolitica* in a product contaminated with the pathogen, said medium having an effective amount of a composition comprising:

(a) a proteolytic digest of protein;

(b) an extract selected from a yeast extract and a beef extract;

(c) an alkali metal chloride or alkaline earth metal chloride; .

(d) bile salts, sodium deoxycholate or sodium cholate; and (e) 5-chloro-2-(2,4-dichlorophenoxy) phenol.

In a more preferred aspect, the invention provides a medium as hereinabove defined further comprising one or more compounds selected from the group consisting of an oxalate salt, a phosphate salt, pyruvic acid, an amino acid, a carbon source, a sulphate salt, sulphonilic acid and 4-(aminocarbonyl)-1-[[2-carboxy-8-oxo-7-[(phenylsulfoacetyl)amino]-5-thia-1-azabicyclo-[4.2.0]oct-2-en-3-yl]methyl]pyridinium hydroxide inner salt;

5-Chloro-2-(2,4-dichlorophenoxy) phenol has the common name, triclosan, and 4-(aminocarbonyl)-1-[[2-carboxy-8-oxo-7-[(phenylsulfoacetyl)amino]-5-thia-1-azabicyclo-[4.2.0]oct-2-en-3-yl]methyl]pyridinium hydroxide inner salt has the common name cefsulodin; which common names will be used throughout this disclosure.

Although triclosan is effective according to the present invention in suppressing the growth of many contaminating microorganisms, most surprisingly, I have found that the combination of triclosan and cefsulodin produces a synergistic effect that suppresses the growth of a further two contaminant microorganisms, namely, Ps. aeruginosa and *A. hydrophila*.

The aqueous solutions of use in the practice of the invention comprise the ingredients as herein defined in amounts which may be readily determined by the person skilled in the art without undue experimentation. By way of guidance, preferred amounts may be selected as follows, viz:

| | |
|---|---|
| 2.0-50.0 g/L | peptone |
| 0.5-50.0 g/L | yeast extract or beef extract |
| 0.5-5.0 g/L | sodium chloride or potassium chloride or calcium chloride or magnesium chloride |
| 0.5-5.0 g/L | bile salts or sodium deoxycholate or sodium cholate |
| 0.01-0.001 g/L | triclosan |

Peptone is a general term for proteolytic digests of protein. One specific peptone of preferred use in the practice of the invention is POLYPEPTONE TM peptone (Becton DiCkenson, Cockeysville, Md., U.S.A.).

Preferably, the pH of the solutions of the invention are adjusted to be in the range of 6.2 to 9.0, more preferably 7.2 to 7.9 and still more preferably 7.6.

The pH may be readily adjusted by the addition of a suitable base, such as sodium hydroxide, or an acid such as phosphoric, hydrochloric or sulphuric acids.

I have found that judicious selection and additions of further ingredients results in increased efficacy. Thus, a most preferred medium of the present invention comprises an aqueous solution of 20 g/L POLYPEPTONE TM peptone
2 g/L yeast extract
2 g/L sodium chloride
0.002 g/L triclosan
1 g/L sodium deoxycholate
10 g/L disodium hydrogensphosphate
2 g/L sodium oxalate
2 g/L pyruvic acid
0.5 g/l glycine
0.01 g/L magnesium sulphate
0.005 g/L ferrous ammonium sulphate
10 g/L sucrose
0.005 g/L cefsulodin; said solution having a pH selected from 7.2 to 7.9.

The invention thus provides a selective enrichment broth medium for isolation of *Y. enterocolitica*. The medium has been tested for the recovery and growth of *Y. enterocolitica* covering a wide range of pathogenic serotypes and non-pathogenic serotypes. The medium has also been studied for its growth inhibition against a number of other common Gram-negative bacteria.

In a further aspect the invention provides a solid composition for use in an aqueous growth medium for enhancing growth of the pathogen which solid composition may be readily prepared by dry-mixing the desired ingredients.

The aqueous formulation of the invention may be readily made by dissolving the desired ingredients, individually, or as a dry-mix to water, followed by sterilization through boiling or autoclave.

The pH of the mediums should be adjusted to 7.6, preferably by addition of NaOH. The medium should be boiled with stirring for 2 minutes, cooled down to room temperature and a solution of Cefsulodin in water added with mixing.

For the recovery of *Y. enterocolitica* from food samples suspected to have less than 10 cells/g or from frozen samples stored under stressed conditions, pre-enrichment of the samples (10% inoculum) at 10° C. for 3 days in modified trypticase soy broth at pH 7.6 and hereinbelow described is preferred. Excellent results have been obtained prior to up 1% inoculation into *Y. enterocolitica* selective enrichment broth.

The composition of the modified trypticase soy broth comprises trypticase soy broth, yeast extract, bile salts, magnesium sulphate, pyruvic acid and sugar (pH 7.6), with incubation temperature of 10° C. for 3 days.

For the recovery of *Y. enterocolitica* from food samples suspected to have at least 10 unstressed cells/g, excellent results have been obtained by direct inoculation of up to 10% into *Y. enterocolitica* selective enrichment broth.

In a yet further aspect, the invention thus provided an assay for determining the presence of *Y. enterocolitica* in a product containing said *Y. enterocolitica*, said assay comprising the step of incubating said product in an aqueous growth medium having an effective amount of an aqueous composition comprising (a) a peptone;
(b) an extract selected from a yeast extract and a beef extract;
(c) an alkali metal chloride or alkaline earth metal chloride;
(d) bile salts or sodium deoxycholate or sodium cholate; and
(e) triclosan.

In a preferred aspect the invention provides an assay for determining the presence of *Y. enterocolitica* in a product containing said *Y. enterocolitica*, said assay comprising the steps of (a) incubating said product in an aqueous growth medium having a composition comprising an effective amount of trypticase soy broth, yeast extract, magnesium sulphate, pyruvic acid and sucrose, at a pH selected from 7.2 to 7.9 to provide an enriched solution of *Y. enterocolitica*; and
(b) incubating said enriched solution in an aqueous *Y. enterocolitica* growth-enhancing composition comprising an effective amount of an aqueous solution as hereinabove defined.

DESCRIPTION OF PREFERRED EMBODIMENTS

In order that the invention may be better understood, preferred embodiments will now be described by way of example only with reference to the following Examples. The results support the improved efficacy of the present invention for the recovery of *Y. enterocolitica* and its superiority over known procedures and media developed to date reported in the literature.

GENERAL

Recovery of *Y. Enterocolitica* From Food Samples

Food, milk and water samples were artificially contaminated with $10^5$ cells/g of five different Gram-negative bacteria and $10^1$ cells/g of different strains of *Y.* enterocolitica representing six serogroups and some standard strains. Ten grams of the contaminated food samples were inoculated into 90 ml of modified TSB and incubated at 10° C. for 3 days. One ml of the cold enriched sample was inoculated into 99 ml of *Yersinia* selective enrichment broth (YSEB) according to the invention and incubated at 22° C. for 1–3 days. Recovery of *Y. enterocolitica* was compared with cold enrichment in TSB at 4° C. for 14 days.

All the strains of different serogroups were recovered by modified TSB and YSEB. On the other hand, the recovery of *Y. entercolitica* was very poor by cold enrichment in TSB at 4° C. for 14 days.

EXAMPLE 1

An aqueous composition according to the invention consisting of the following ingredients in the stated amounts of grams per liter was prepared by the addition thereof to water.

20 g/L POLYPEPTONE TM peptone
2 g/L yeast extract
2 g/L sodium chloride
0,002 g/L triciosan
1 g/L sodium deoxycholate
10 g/L disodium hydrogen phosphate
2 g/L sodium oxalate
2 g/L pyruvic acid
0.5 g/L glycine
0.01 g/L magnesium sulphate
0.005 g/L ferrous ammonium sulphate
10 g/L sucrose
0.005 g/L cefsulodin; the solution having a pH of 7.6.

EXAMPLE 2

The following aqueous composition according to the invention was prepared in a similar manner as for Example 1.

20 g/L POLYPEPTONE TM peptone
2 g/L yeast extract
2 g/L sodium chloride
0. 002 g/L triclosan
1 g/L sodium deoxycholate
10 g/L disodium hydrogen phosphate
2 g/L sodium oxalate
2 g/L pyruvic acid
0.5 g/L glycine
0.01 g/L magnesium sulphate
0.005 g/L ferrous ammonium sulphate
0.005 g/L cefsulodin; the solution having a pH of 7.6.

EXAMPLE 3

The following aqueous composition according to the invention was prepared in a similar manner as for Example 1.

20 g/L POLYPEPTONE TM peptone
2 g/L yeast extract
2 g/L sodium chloride
0.002 g/L triclosan
1 g/L sodium deoxycholate
10 g/L disodium hydrogen phosphate
2 g/L sodium oxalate
2 g/L pyruvic acid
0.5 g/L glycine
0.01 g/L magnesium sulphate
0.005 g/L ferrous ammonium sulphate; the solution having a pH of 7.6.

EXAMPLE 4

Comparative studies with alternative antimicrobial agents were carried out using the medium of Example 1 but with the triclosan substituted with such other antimicrobial agent. The results are presented in TABLE 7.

RESULTS

In the following tables the +'s and −'s denote, unless otherwise indicated, the following:

++++ = $>10^8$ cells/ml
+++ = $10^7$–$10^8$ cells/ml
++ = $10^5$–$10^6$ cells/ml
+ = $<10^{-4}$ cells/ml
± = 1 strain of microorganism is inhibited
− = all microorganism strains were inhibited
nd = not done Table 1 shows the results for the recovery of *Y. enterocolitica* in the medium according to the invention defined in Example 1 at low initial cell count of $10^1$/ml at 25° C. after 24 hours and 48 hours.

TABLE 1

| Microorganism | Initial CFU/ml in proposed medium | CFU/ml after 24 h of incubation | CFU/ml after 48 h of incubation |
|---|---|---|---|
| *Y. enterocolitica* 0:3 | 28.3 | $10^7$ | $10^9$ |
| *Y. enterocolitica* 0:3 | 39.0 | $10^5$ | $10^9$ |
| *Y. enterocolitica* 0:3 | 50.0 | $10^7$ | $10^9$ |
| *Y. enterocolitica* 0:5,27 | 18.0 | $10^5$ | $10^9$ |
| *Y. enterocolitica* 0:5,27 | 60.0 | $10^7$ | $10^9$ |
| *Y. enterocolitica* 0:5,27 | 42.3 | $10^8$ | $10^9$ |
| *Y. enterocolitica* 0:6,30 | 30.0 | $10^8$ | $10^9$ |
| *Y. enterocolitica* 0:6,30 | 38.2 | $10^8$ | $10^9$ |
| *Y. enterocolitica* 0:6,30 | 26.0 | $10^8$ | $10^9$ |
| *Y. enterocolitica* 0:8 | 40.0 | $10^8$ | $10^9$ |
| *Y. enterocolitica* 0:8 | 47.0 | $10^7$ | $10^9$ |
| *Y. enterocolitica* 0:8 | 56.0 | $10^3$ | $10^9$ |
| *Y. enterocolitica* 0:9 | 40.0 | $10^7$ | $10^9$ |
| *Y. enterocolitica* 0:9 | 45.0 | $10^7$ | $10^9$ |
| *Y. enterocolitica* 0:6,31 | 27.0 | $10^8$ | $10^9$ |
| *Y. enterocolitica* 0:6,31 | 62.0 | $10^7$ | $10^9$ |
| *Y. enterocolitica* 0:6,31 | 61.0 | $10^8$ | $10^9$ |
| *Y. enterocolitica* ATCC 27729 | 50.0 | $10^3$ | $10^9$ |
| *Y. enterocolitica* ATCC 23715 | 11.0 | $10^5$ | $10^9$ |

CFU = Colony Forming Unit

Table 2 shows the recovery of *Y. enterocolitica* in the medium of Example 1 at low initial cell count of 2–8 cells/ml at 25° C. after 24 hours and 48 hours.

TABLE 2

| Microorganism | Initial CFU/ml in proposed medium | CFU/ml after 24 h of incubation | CFU/ml after 48 h of incubation |
|---|---|---|---|
| *Y. enterocolitica* 0:3 | 2.8 | $10^4$ | $10^9$ |
| *Y. enterocolitica* 0:3 | 3.9 | $10^4$ | $10^9$ |
| *Y. enterocolitica* 0:3 | 5.0 | $10^4$ | $10^9$ |
| *Y. enterocolitica* 0:5,27 | 1.8 | $10^4$ | $10^9$ |
| *Y. enterocolitica* 0:5,27 | 6.0 | $10^5$ | $10^9$ |
| *Y. enterocolitica* 0:5,27 | 4.23 | $10^6$ | $10^9$ |
| *Y. enterocolitica* 0:6,30 | 3.0 | $10^7$ | $10^9$ |
| *Y. enterocolitica* 0:6,30 | 3.8 | $10^7$ | $10^9$ |
| *Y. enterocolitica* 0:6,30 | 2.6 | $10^7$ | $10^9$ |
| *Y. enterocolitica* 0:8 | 4.0 | $10^7$ | $10^9$ |
| *Y. enterocolitica* 0:8 | 4.7 | — | — |
| *Y. enterocolitica* 0:8 | 5.6 | — | — |
| *Y. enterocolitica* 0:9 | 4.0 | $10^5$ | $10^9$ |
| *Y. enterocolitica* 0:9 | 4.5 | $10^5$ | $10^9$ |
| *Y. enterocolitica* 0:6,31 | 2.7 | $10^7$ | $10^9$ |
| *Y. enterocolitica* 0:6,31 | 6.2 | $10^3$ | $10^9$ |
| *Y. enterocolitica* 0:6,31 | 6.1 | $10^7$ | $10^9$ |
| *Y. enterocolitica* ATCC 27729 | 5.0 | — | — |
| *Y. enterocolitica* ATCC 23715 | 1.1 | $10^2$ | $10^9$ |

CFU = Colony Forming Unit

Table 3 shows the results of the growth of Gram-negative bacteria in trypticase soy broth (TSB) and Yersinia selective enrichment broth YSEB at initial cell count of $10^3$–$10^4$/ml at 22° C. in 24 hours.

TABLE 3

| Microorganism | Number of strains tested | Growth in TSB | Growth in YSEB |
|---|---|---|---|
| *Aeromonas hydrophila* | 1 | + | – |
| *Citrobacter amalonaticus* | 1 | + | – |
| *Enterobacter agglomerans* | 1 | + | – |
| *Enterobacter cloacae* | 2 | + | – |
| *Escherichia coli* | 7 | + | – |
| *Hafnia alvel* | 1 | + | – |
| *Klebsiella pneumoniae* | 1 | + | – |
| *Morganella morganii* | 1 | + | + |
| *Proteus mirabilis* | 1 | + | – |
| *Proteus vulgaris* | 1 | + | – |
| *Pseudomonas aeruginosa* | 1 | + | – |
| *Salmonelia arizonae* | 1 | + | – |
| *Salmonelia typhimurium* | 2 | + | – |
| *Salmonelia enteritidis* | 1 | + | – |
| *Salmonelia hadar* | 1 | + | – |
| *Salmonella heidelberg* | 1 | + | – |
| *Salmonella Senftenherg* | 1 | + | – |
| *Shigelia sonnei* | 1 | + | – |
| *Serratia liquefaciens* | 1 | + | + |

\+ = Growth
– = No Growth

Table 4 shows the summary of growth results obtained in the medium according to the invention defined in Example 1.

TABLE 4

| Microorganism | Growth |
|---|---|
| *Y. enterocolitica* 0:3 | ++++ |
| *Y. enterocolitica* 0:5,27 | ++++ |
| *Y. enterocolitica* 0:6,30 | ++++ |
| *Y. enterocolitica* 0:8 | ++++ |
| *Y. enterocolitica* 0:9 | ++++ |
| *Y. enterocolitica* 0:6,31 | ++++ |
| *Ps. aeruginosa* | – |
| *Sr. liquefaciens* | ++++ |
| *M. morganii* | ++++ |
| *A. hydrophilla* | – |
| *Pr. mirabilus* | – |
| *Sal. arizona* | – |
| *Pr. vulgaris* | – |
| *E. coli* | – |
| *E. agglumerens* | – |
| *Sh. sonnei* | – |
| *K. pneumoniae* | – |

TABLE 4-continued

| Microorganism | Growth |
|---|---|
| *E. colaca* | – |
| *Sal. typhimurium* | – |

Table 5 shows the results of growth obtained for various microorganisms in the medium according to the invention defined in Example 2.

TABLE 5

| Microorganism | Growth |
|---|---|
| *Y. enterocolitica* 0:3 | +++ |
| *Y. enterocolitica* 0:5,27 | +++ |
| *Y. enterocolitica* 0:6,30 | +++ |
| *Y. enterocolitica* 0:8 | +++ |
| *Y. enterocolitica* 0:9 | +++ |
| *Y. enterocolitica* 0:6,31 | +++ |
| *Ps. aeruginosa* | – |
| *Sr. liquefaciens* | +++ |
| *M. morganii* | +++ |
| *A. hydrophilla* | – |
| *Pr. mirabilus* | – |
| *Sal. arizona* | – |
| *Pr. vulgaris* | – |
| *E. coli* | – |
| *E. agglumerens* | – |
| *Sh. sonnei* | – |
| *K. pneumoniae* | – |
| *E. colaca* | – |
| *Sal. typhimurium* | – |

Table 6 shows the results of growth of various microorganisms in the medium according to the invention defined in Example 3.

TABLE 6

| Microorganism | Growth |
|---|---|
| *Y. enterocolitica* 0:3 | +++ |
| *Y. enterocolitica* 0:5,27 | +++ |
| *Y. enterocolitica* 0:6,30 | +++ |
| *Y. enterocolitica* 0:8 | +++ |
| *Y. enterocolitica* 0:9 | +++ |
| *Y. enterocolitica* 0:6,31 | +++ |
| *Ps. aeruginosa* | ++ |
| *Sr. liquefaciens* | +++ |
| *M. morganii* | +++ |
| *A. hydrophilla* | – |
| *Pr. mirabilus* | – |
| *Sal. arizona* | – |
| *Pr. vulgaris* | – |
| *E. coli* | – |

TABLE 6-continued

| Microorganism | Growth |
|---|---|
| *E. agglumerens* | − |
| *Sh. sonnei* | − |
| *K. pneumoniae* | − |
| *E. colaca* | − |
| *Sal. typhimurium* | − |

Table 7 shows results of growth of several serotypes of *Y. enteroclitica* and of several other microorganisms in media comprising an antimicrobial agent. The table clearly shows the surprising selective antimicrobial activity of triclosan against these microorganisms.

TABLE 7

| ANTIMICROBIAL | MICROORGANISM | | | | | | | | | | |
|---|---|---|---|---|---|---|---|---|---|---|---|
| AGENT | A | B | C | D | E | F | G | H | I | J | K |
| TICARCILLIN (2 μ/ml) | +++ | +++ | +++ | +++ | +++ | ND | +++ | +++ | +++ | +++ | ND |
| CARBENICILLIN (1 μ/ml) | +++ | ++ | +++ | +++ | +++ | ND | +++ | +++ | +++ | +++ | ND |
| OLEANDOMYCIN (10 μ/ml) | +++ | +++ | +++ | +++ | +++ | ND | +++ | +++ | +++ | +++ | ND |
| ROXARSONE (100 μ/ml) | +++ | +++ | +++ | +++ | +++ | ND | +++ | +++ | +++ | +++ | ND |
| SULFADIAZINE (40 μ/ml) | ++ | ± | + | + | − | ND | ++ | ++ | ++ | ++ | ++ |
| ALIZARIN (100 μ/ml) | +++ | +++ | +++ | +++ | +++ | +++ | + | +++ | +++ | +++ | +++ |
| JOSAMYCIN (20 μg/ml) | + | ++ | +++ | +++ | +++ | +++ | +++ | +++ | +++ | +++ | +++ |
| CYCLOSERINE (70 μ/ml) | ++ | ++ | ++ | ++ | ++ | ++ | + | +++ | +++ | +++ | +++ |
| POTASSIUM CHLORATE (1 mg/ml) | ++ | ++ | ++ | ++ | ++ | +++ | +++ | +++ | +++ | ND | +++ |
| NOVOBIOCIN (2.5 μ/ml) | +++ | +++ | +++ | +++ | +++ | +++ | +++ | +++ | +++ | +++ | +++ |
| GLYCINE (5 mg/ml) | +++ | ++ | ++ | ++ | ++ | ++ | ++ | +++ | +++ | ND | +++ |
| SODIUM THIOSULFATE (0.68%) | ++ | ++ | ++ | ++ | ++ | ND | + | +++ | +++ | ND | ND |
| SODIUM DODECYL SULFATE (1%) | − | − | − | − | − | ND | − | − | − | ND | ND |
| FERRIC AMMONIUM CITRATE (0.08%) | ++ | + | ++ | ++ | +++ | ND | + | +++ | +++ | ND | ND |
| TRICLOSAN | ++++ | ++++ | ++++ | ++++ | ++++ | ++++ | | − | − | − | − |

wherein:
Microorganism:
A = *Y. enterocolitica* 0:3 (3)[a]
B = *Y. enterocolitica* 0:5,27 (3)
C = *Y. enterocolitica* 0:6,30 (3)
D = *Y. enterocolitica* 0:8 (3)
E = *Y. enterocolitica* 0:9 (2)
F = *Y. enterocolitica* 0:6,31 (3)
G = *Ps. aeruginosa* (1)
H = *Sr. liquefaciens* (1)
I = *M. morganii* (1)
J = *Pr. vulgaris* (1)
K = *A. hydrodhila* (1)
[a]The number in parenthesis is the number of strains studied Table 8 shows a list of combinations of antimicrobial agents found to be ineffective in satisfying the objects of the present invention.

TABLE 8

| | MICROORGANISM | | | | | | | | | |
|---|---|---|---|---|---|---|---|---|---|---|
| ANTIMICROBIAL AGENT | K | I | H | G | F | E | D | C | B | A |
| Irgasan (4 μg/ml) + Ticarcillin (2 μg/ml) + Oleandomycin (10 μg/ml) + Roxanson (100 μ/ml) | ND | +++ | − | +++ | ND | +++ | +++ | +++ | − | + |
| Sulfanilic acid (10 μg/ml) + Irgasan (4 μg/ml) | ND | +++ | +++ | +++ | ND | ++ | ++ | ++ | ++ | ++ |
| Toluidine (5 μg/ml) + Irgasan (4 μg/ml) | ND | +++ | +++ | +++ | ND | ++ | ++ | +++ | ++ | ++ |
| Sodium sulfite (0.5%) + Irgasan (4 μg/ml) | ND | ++ | ++ | ++ | ND | + | + | − | − | − |
| Sulfadiazine (40 μg/ml) + Irgasan (4 μg/ml) | ++ | ++ | + | − | ± | − | − | + | ± | + |
| Sulfapyridine (40 μg/ml) + Irgasan (4 μg/ml) | +++ | +++ | +++ | − | ++ | + | +++ | +++ | ± | ++ |
| Vancomycin 50 μg/ml + Irgasan 4 mg/ml | ++ | ++ | +++ | + | +++ | − | +++ | +++ | − | − |
| Metanile Yellow 1 mg/ml + Irgasan 4 μg/ml | ++ | ++ | +++ | + | + | − | + | + | − | − |
| Alizarin 25 μg/ml + Irgasan 4 μg/ml | + | + | ++ | + | ± | − | ++ | ± | − | − |

TABLE 8-continued

| ANTIMICROBIAL AGENT | MICROORGANISM K | I | H | G | F | E | D | C | B | A |
|---|---|---|---|---|---|---|---|---|---|---|
| Josamycin 20 μg/ml + Irgasan | + | + | + | + | + | + | + | + | + | + |
| 4 μg/ml | + | + | + | + | + | + | + | + | + | |
| | + | + | + | | + | + | + | + | | |
| Novobiocin 2.5 μg/ml + | − | + | + | − | + | + | + | + | ± | + |
| Cefsulodin 10 μg/ml + Irgasan | | + | + | | + | + | + | + | | |
| 4 μg/ml | | | | | | | | + | | |
| Cycloserine 50 μg/ml + Irgasan | + | + | + | + | + | + | + | + | ± | + |
| 4 μg/ml | + | + | + | | + | + | + | + | | + |
| | | | | | + | + | | + | | |
| Potassium chlorate 2 mg/ml + | + | + | + | + | + | + | + | + | ± | + |
| Irgasan 4 μg/ml | + | + | + | + | + | + | + | + | | |
| | + | + | + | | + | | + | | | |
| Glycine 0.5% + Irgasan 4 μg/ml | + | + | + | + | + | + | + | + | ± | + |
| | + | + | + | | + | + | + | + | | + |
| Bile slats 0.1% + Glycine | + | + | + | − | + | + | + | + | + | + |
| 0.5 mg/ml | + | + | + | | + | + | + | + | + | + |
| | | + | + | | | | | | | + |
| Glycine 0.5% + Bile Salts 0.2% + | + | + | + | + | + | + | + | + | + | + |
| Irgasan 2 μg/ml | | + | + | | + | + | + | + | + | + |
| | | + | + | | | | | | | |
| Glycine 0.3% + Sodium chloride | + | + | + | + | + | + | + | + | + | + |
| 0.5% + Irgasan 4 μg/ml | + | + | + | | + | + | + | + | + | + |
| | + | + | + | | + | + | + | + | | |

A = *Y. enterocolitica* 0:3 (3)[a]
B = *Y. enterocolitica* 0:5,25 (3)
C = *Y. enterocolitica* 0:6,30 (3)
D = *Y. enterocolitica* 0:8 (3)
E = *Y. enterocolitica* 0:9 (2)
F = *Y. enterocolitica* 0:6,31 (3)
G = *Ps. aeruginose* (1)
H = *Sr. liquefaciens* (1)
I = *M. morganii* (1)
K = *A. hydrophila* (1)

Although this disclosure has described preferred embodiments of the invention, it is to be understood that the invention is not restricted to these particular embodiments. Rather, the invention includes all embodiments which are functional or chemical equivalents of the specific embodiments and features that have been described.

I claim:

1. A medium for selectively enhancing the growth of the pathogen *Yersinia enterocolitica* in a product contaminated with the pathogen, comprising an aqueous solution of 20 g/L peptone
2 g/L yeast extract
2 g/L sodium chloride
0.002 g/L triclosan
1 g/L sodium deoxycholate
10 g/L disodium hydrogen phosphate
2 g/L sodium oxalate
2 g/L pyruvic acid
0.5 g/L glycine
0.01 g/L magnesium sulphate
0.005 g/L ferrous ammonium sulphate
10 g/L sucrose
0.005 g/L cefsulodin; said solution having a pH selected from 7.2 to 7.9.

2. An assay for determining the presence of *Yersinia enterocolitica* in a product containing said *Y. enterocolitica*, said assay comprising the steps of (a) incubating said product in an aqueous growth medium having a composition comprising an effective amount of trypticase soy broth, yeast extract, a magnesium salt, pyruvic acid and sucrose, at a pH selected from 7.2 to 7.9 to provide an enriched solution of *Y. enterocolitica*; and (b) Incubating said, enriched solution in an aqueous *Y. enterocolitica* growth enhancing composition comprising a *Y. enterocolitica* growth enhancing amount of a composition as defined in claim 1.

* * * * *